United States Patent [19]

Yagita

[11] Patent Number: 5,708,037
[45] Date of Patent: Jan. 13, 1998

[54] INHIBITOR OF INFLAMMATORY CYTOKINE FORMATION COMPRISING POLYPRENYL DERIVATIVES AS THE ACTIVE INGREDIENT

[75] Inventor: Akikuni Yagita, Mitaka, Japan

[73] Assignee: Sankyo Company, Limited, Tokyo, Japan

[21] Appl. No.: 656,576

[22] Filed: May 31, 1996

Related U.S. Application Data

[63] Continuation of PCT/JP94/01971, Nov. 23, 1994.

[30] Foreign Application Priority Data

Dec. 1, 1993 [JP] Japan .................... 5-300751

[51] Int. Cl.$^6$ .................... A61K 31/05; A61K 31/225
[52] U.S. Cl. .................... 514/735; 514/547
[58] Field of Search .................... 514/547, 735

[56] References Cited

U.S. PATENT DOCUMENTS 4,192,953  3/1980  Mishima et al. .
4,434,179  2/1984  Kobayashi et al. .

Primary Examiner—Raymond Henley, III
Attorney, Agent, or Firm—Frishauf, Holtz, Goodman, Langer & Chick, P.C.

[57] ABSTRACT

Polyprenyl derivatives having the general formula as the active ingredient:

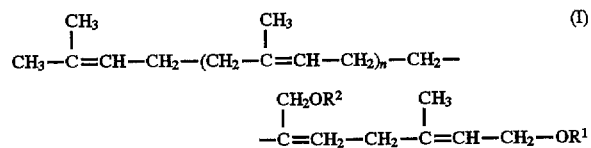

where $R^1$ and $R^2$ are the same or different, and each represents a hydrogen atom, a $C_1$–$C_4$ alkyl group, a $C_2$–$C_{12}$ aliphatic acyl group, a $C_7$–$C_{11}$ aromatic acyl group or a $C_8$–$C_{12}$ aryl-substituted aliphatic acyl group; and n represents an integer from 0 to 2, show excellent activity in the inhibition of the formation of inflammatory cytokines, and they exhibit an excellent therapeutic effect on inflammatory bowel diseases such as ulcerative colitis, Crohn's disease and Behcet syndrome.

17 Claims, No Drawings

INHIBITOR OF INFLAMMATORY CYTOKINE FORMATION COMPRISING POLYPRENYL DERIVATIVES AS THE ACTIVE INGREDIENT

This application is a continuation application of International application PCT/JP94/01971 filed Nov. 22, 1994 (Chapter II).

TECHNICAL FIELD

The present invention concerns an inhibitor of inflammatory cytokine formation comprising polyprenyl derivatives as the active ingredient, and a method for the prophylaxis and/or treatment of diseases, which method is based on the inhibition of inflammatory cytokine formation by use of polyprenyl derivatives as the active ingredient.

TECHNICAL BACKGROUND

Inflammatory bowel diseases include ulcerative colitis and Crohn's disease. In both of these diseases, intractable ulceration or inflammation occurs in the intestinal tract of a young adult, and each is designated as one of the intraceable diseases in this country.

Inflammatory bowel diseases occur frequently in the developed countries in Europe and America, and their sudden increase has also been observed in this country. A therapeutic method for these diseases has not yet been established, with the lone exception of a finding that sulfasalazine or asteroid derivative such as prednisolone is partly effective.

On the other hand, Behcet syndrome is a disease showing four main symptoms, stomatitis, skin symptoms, pudendal ulcer and eye symptoms. A disease showing the above four symptoms and having additional intestinal symptoms is known as intestinal type Behcet syndrome. These four main symptoms are convenient for diagnosis. However, these do not directly cause direct death, the main cause of death from Behcet syndrome being peritonitis caused by intestinal perforation.

Accompanied by the recent progress of immunology and gene manipulation, it is becoming clear that inflammatory cytokines including tumor necrotizing factor-α (hereinafter, abbreviated to TNFα) interleukine-6 (hereinafter, abbreviated to IL-6) and interleukine-8 (hereinafter, abbreviated to IL-8) participate in the cause and aggravation of these inflammatory bowel diseases and Behcet syndrome: in more detail, it is found that formation of these inflammatory cytokines is increased at the injured sites. Therefore, it is considered that inhibition of the formation of these inflammatory cytokines may be useful for the therapy and prevention of inflammatory bowel diseases and Behcet syndrome.

As mentioned above, the development of a drug having an excellent activity in inhibiting the formation of inflammatory cytokines and which is useful for the therapy and prevention of inflammatory bowel diseases and Behcet syndrome has been desired.

DISCLOSURE OF THE PRESENT INVENTION

The present inventors studied the pharmacological activities of various polyprenyl derivatives for many years. Their study resulted in the discovery that certain polyprenyl derivatives have an excellent activity in inhibiting the formation of inflammatory cytokines and they exhibit an excellent therapeutic effect on inflammatory bowel diseases including ulcerative colitis and Crohn's disease and on Behcet syndrome, and they have low toxicity; and that these derivatives are useful as an agent for inhibiting inflammatory cytokine formation and as a therapeutic and preventive agent for inflammatory bowel diseases and Behcet syndrome; and this resulted in completion of the present invention. Although the polyprenyl derivatives of the present invention are known to have antiulcer activity (for example, Japanese Patent Application Kokai No. Sho 52-62213 etc.,), their activity in inhibiting the formation of inflammatory cytokines, their therapeutic effect on inflammatory bowel diseases etc., are not known.

CONSTITUTION OF INVENTION

The polyprenyl derivatives, the active ingredient of the present invention, have the general formula:

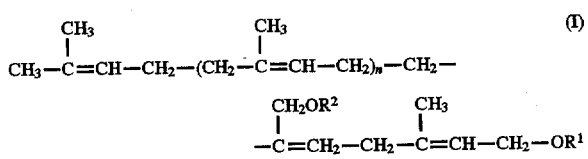

In the formula above:

$R^1$ and $R^2$ are the same or different, and each represents a hydrogen atom, a $C_1$–$C_4$ alkyl group, a $C_2$–$C_{12}$ aliphatic acyl group, a $C_7$–$C_{11}$ aromatic acyl group or a $C_8$–$C_{12}$ aryl-substituted aliphatic acyl group; and n represents an integer from 0 to 2.

The $C_1$–$C_4$ alkyl group may be, for example, a methyl, ethyl, propyl, isopropyl, butyl, sec-butyl or isobutyl group; preferably a $C_1$–$C_2$ alkyl group; and particularly preferably a methyl group.

The $C_2$–$C_{12}$ aliphatic acyl group may have double bond(s) and may be an acetyl, propionyl, butyryl, valeryl, isovaleryl, caproyl, heptanoyl, octanoyl, nonanoyl, decanoyl, lauroyl, acryloyl, metacryloyl, crotonoyl or 3-butenoyl group; preferably a $C_2$–$C_6$ aliphatic acyl group and particularly preferably an acetyl group.

The $C_7$–$C_{11}$ aromatic acyl group may be, for example, a benzoyl or naphtoyl group; preferably a benzoyl group. The aromatic acyl group may have substituent(s) on the ring; and the substituent may be the aforementioned $C_1$–$C_4$ alkyl group; a $C_1$–$C_4$ alkoxy group such as a methoxy, ethoxy, propoxy, isopropoxy or butoxy group; or a halogen atom such as a fluorine, chlorine, bromine or iodine atom; preferably a methyl, methoxy, fluorine or chlorine atom.

The $C_8$–$C_{12}$ aryl-substituted aliphatic acyl group may have double bond, and may be a phenylacetyl, phenylpropionyl, phenylbutyryl, phenylvaleryl, naphthylacetyl or cinnamoyl group; preferably a phenylacetyl or cinnamoyl group; and particularly preferably a cinnamoyl group. The aryl-substituted aliphatic acyl group may have substituent(s) on the ring; and the substituents may be the same substituents as mentioned already for the aromatic acyl group.

In compound (I), there are geometric isomers due to the double bond in the molecule. The scope of the active ingredient of the present invention covers all these isomers, and preferable isomers are those in which all the double bonds have a trans configuration.

Of the compounds having the general formula (I) mentioned above, the following may be mentioned as preferable ones, in which:

(1) $R^1$ and $R^2$ are the same, and each represents a hydrogen atom, a methyl group, a $C_2$–$C_{12}$ aliphatic acyl group, a benzoyl group or a cinnamoyl group;

(2) $R^1$ and $R^2$ are the same, and each represents a hydrogen atom or a $C_2$-$C_6$ aliphatic acyl group;

(3) $R^1$ and $R^2$ are the same, and each represents a hydrogen atom or an acetyl group;

(4) $R^1$ and $R^2$ are the same, and each represents a hydrogen atom; and (5) n is 1.

In addition, a compound in which the groups are combined with ones selected optionally from the groups (1) to (5) may be also preferable.

Preferred compounds represented by the general formula (I) may be exemplified concretely in the following Table 1.

TABLE 1

| Compound No. | $R^1$ | $R^2$ | n |
|---|---|---|---|
| 1 | H | H | 0 |
| 2 | Me | Me | 0 |
| 3 | MeCO | MeCO | 0 |
| 4 | EtCO | EtCO | 0 |
| 5 | PrCO | PrCO | 0 |
| 6 | $C_5H_{11}CO$ | $C_5H_{11}CO$ | 0 |
| 7 | $C_{11}H_{23}CO$ | $C_{11}H_{23}CO$ | 0 |
| 8 | $CH_2$=CHCO | $CH_2$=CHCO | 0 |
| 9 | CH(Me)=CHCO | CH(Me)=CHCO | 0 |
| 10 | PhCO | PhCO | 0 |
| 11 | PhCH=CHCO | PhCH=CHCO | 0 |
| 12 | H | H | 1 |
| 13 | Me | Me | 1 |
| 14 | Et | Et | 1 |
| 15 | MeCO | MeCO | 1 |
| 16 | H | MeCO | 1 |
| 17 | EtCO | EtCO | 1 |
| 18 | PrCO | PrCO | 1 |
| 19 | i-PrCO | i-PrCO | 1 |
| 20 | BuCO | BuCO | 1 |
| 21 | $C_5H_{11}CO$ | $C_5H_{11}CO$ | 1 |
| 22 | $C_{11}H_{23}CO$ | $C_{11}H_{23}CO$ | 1 |
| 23 | $CH_2$=CHCO | $CH_2$=CHCO | 1 |
| 24 | $CH_2$=C(Me)CO | $CH_2$=C(Me)CO | 1 |
| 25 | CH(Me)=CHCO | CH(Me)=CHCO | 1 |
| 26 | PhCO | PhCO | 1 |
| 27 | 4-Me-PhCO | 4-Me-PhCO | 1 |
| 28 | PhCH=CHCO | PhCH=CHCO | 1 |
| 29 | H | H | 2 |
| 30 | Me | Me | 2 |
| 31 | MeCO | MeCO | 2 |
| 32 | EtCO | EtCO | 2 |
| 33 | PrCO | PrCO | 2 |
| 34 | $C_5H_{11}CO$ | $C_5H_{11}CO$ | 2 |
| 35 | $C_{11}H_{23}CO$ | $C_{11}H_{23}CO$ | 2 |
| 36 | $CH_2$=CHCO | $CH_2$=CHCO | 2 |
| 37 | CH(Me)=CHCO | CH(Me)=CHCO | 2 |
| 38 | PhCO | PhCO | 2 |
| 39 | PhCH=CHCO | PhCH=CHCO | 2 |

In the above table, the following abbreviations are used:
Bu=butyl
Et=ethyl
Me=methyl
Ph=phenyl
Pr=propyl
i-Pr=isopropyl
In the table above:
Preferred compounds are Compound Nos. 1, 3, 6, 7, 9, 10, 11, 12, 13, 15, 17, 21, 22, 23, 25, 26, 28, 29, 31, 34, 35, 37, 38 and 39;

More preferred compounds are Compound Nos. 1, 3, 12, 13, 15, 21, 22, 25, 26, 28, 29 and 31;

Much more preferred compounds are Compound Nos. 12, 13, 15, 21, 22, 25, 26 and 28;

Yet more preferred compounds are Compound Nos. 12 and 15; and

The particularly preferred compound is No. 12.

The polyprenyl derivatives having the general formula (I), which are the active ingredient of the present invention, are known compounds, or can be prepared easily according to the known methods (for example, Japanese Patent Application Kokai No. Sho 52-62213 etc.).

EFFECT OF INVENTION

The polyprenyl derivatives of the present invention have an excellent activity in inhibiting the formation of inflammatory cytokines, they exhibit an excellent therapeutic effect on inflammatory bowel diseases and Behcet syndrome, and they show low toxicity. Therefore these derivatives are useful as a therapeutic and preventive agent for various kinds of diseases mentioned below, based on their inhibiting effect on the formation of inflammatory cytokines etc.

(1) Inflammatory bowel diseases including ulcerative colitis and Crohn's disease;

(2) Behcet syndrome;

(3) Autoimmune diseases including articular rheumatism, systemic lupus erythematosus (SLE) and diabetes mellitus;

(4) Stomatitis;

(5) Diseases with fistulation;

(6) Organ injuries associated with such diseases as cerebral infarction, pulmonary infarction, myocardial infarction etc., and resultant ischemia;

(7) Organ injuries and tissue injuries accompanied with reperfusion; and (8) Rejection reactions in organ transplantation etc.

Among these diseases, polyprenyl derivatives having the general formula (I), which are the active ingredient of the present invention, are preferably useful as a therapeutic and prophylatic agent for inflammatory bowel diseases or for Behcet syndrome, more preferably as a therapeutic and preventive agent for inflammatory bowel diseases, and particularly preferably as a therapeutic and preventive agent for ulcerative colitis and Crohn's disease.

POSSIBLE USAGE IN INDUSTRY

As mentioned above, polyprenyl derivatives having the general formula (I), which are the active ingredient of the present invention, have an excellent activity in inhibiting the formation of inflammatory cytokines, they exhibit an excellent therapeutic effect on inflammatory bowel diseases and Behcet syndrome, and they are useful as a therapeutic and prophylactic agent for inflammatory bowel diseases.

When the polyprenyl derivatives having the general formula (I), which are the active ingredient of the present invention, are used as an agent for inhibiting inflammatory cytokine formation, the derivatives by themselves or a mixture of the derivatives and any pharmaceutically acceptable carriers, vehicles, diluents etc., may be administered orally or parenterally (including intrarectal administration) as pharmaceutical compositions such as powders, granules, tablets, capsules, injections, suppositories etc., and preferably orally. Though the dosage may be varied depending on the disease in question, the condition and age of the patient in question, the mode of administration etc., a dose of from 1 mg to 1000 mg (preferably from 10 mg to 500 mg) in a case of oral administration, and a dose of from 0.1 mg to 500 mg (preferably from 1 mg to 300 mg) in the case of intravenous administration, may be given one to three times a day according to the symptoms.

THE BEST MODE FOR WORKING THE PRESENT INVENTION

Test Examples and Preparation Examples shown below will explain the present invention in more detail. However, these examples do not limit the scope of the present invention.

TEST EXAMPLE 1

Cytokine formation inhibiting Effect

About 30 ml of a peripheral blood sample (to which heparin was added) was taken from each of 3 patients with ulcerative colitis during active stage and 3 patients with Crohn's disease. The samples were separated by their specific gravity using Ficoll-Lonray Percoll to give monocyte (Mo) and macrophage (Mφ) fractions. 10% fetal cow serum (FCS) was added to these fractions and the mixture was prepared to be $1 \times 10^4$ cells/ml, by use of Rosewell Park Memorial Institute medium (RPMI-1640).

100 μl/ml of a known concentration of a test compound [Compound No. 12 (plaunotol): $10^{-5}$M, $10^{-6}$M and $10^{-7}$M; sulfasalazine: $10^{-3}$M, $10^{-4}$M and $10^{-5}$M; prednisolone: $2 \times 10^{-5}$M] was added to the diluted preparation. At that time, 0.01 mg/ml of lipopolysaccharide was added as a stimulant. After incubation for 3 hours under carbon dioxide, the serum cytokine levels were determined by solid phase enzyme-linked immunosorbent assay. The results are shown in Table 2 and Table 3.

TABLE 2

Cytokine formation inhibiting effect in a Mo-Mφ cell system derived from the peripheral blood samples of patients with ulcerative colitis

| Test compounds (Concentration) | Formation rates of cytokines (%) | | |
|---|---|---|---|
| | TNFα | IL-6 | IL-8 |
| Compound No. 12 ($10^{-6}$M) | 54.1 ± 21.2*) | 32.9 ± 3.5**) | 62.8 ± 22.7 |
| Sulfasalazine ($10^{-4}$M) | 55.8 ± 47.0*) | 38.8 ± 8.3**) | 58.5 ± 34.3 |
| Prednisolone ($2 \times 10^{-5}$M) | 32.1 ± 22.3*) | 24.2 ± 6.8**) | 57.0 ± 31.6 |
| Control | 100 | 100 | 100 |

\*)P < 0.05
\*\*)P < 0.01.

TABLE 3

Cytokine formation inhibiting effect in Mo-Mφ cell system derived from the peripheral blood samples of patients with Crohn's disease

| Test compounds (Concentration) | Formation rates of cytokines (%) | | |
|---|---|---|---|
| | TNFα | IL-6 | IL-8 |
| Compound No. 12 ($10^{-6}$M) | 19.9 ± 12.4*) | 29.9 ± 3.9*) | 46.9 ± 5.1*) |
| Sulfasalazine ($10^{-4}$M) | 10.9 ± 18.6*) | 21.6 ± 6.7*) | 44.2 ± 6.6*) |
| Prednisolone ($2 \times 10^{5}$M) | 9.4 ± 16.2*) | 13.8 ± 7.2*) | 33.0 ± 2.7*) |
| Control | 100 | 100 | 100 |

\*)P < 0.01

As shown in these tables above, Compound No. 12 has a significant inhibitory effect, at a concentration of $10^{-6}$M, on the formation of three kinds of cytokines, TNFα, IL-6 and IL-8, in the Mo-Mφ cell systems derived from peripheral blood samples of patients with ulcerative colitis and Crohn's disease (a decreased effect was observed on the levels of IL-8 in the peripheral blood Mo-Mφ cell system derived from patients with ulcerative colitis); and it shows equivalent or greater utility compared to sulfasalazine or prednisolone.

TEST EXAMPLE 2

Clinical Effect in Patients with Ulcerative Colitis

Compound No. 12 was administered to 5 patients with ulcerative colitis (active stage) at a daily dosage of from 3 tablets (240 mg) to 6 tablets (480 mg) divided into 3 doses. The patients were 3 females and 2 males from 21 to 46 years old. Among these patients, 4 cases had not shown improvement even after administration of 6 tablets (3.0 g) a day of sulfasalazine for 3 months, and the other case was incipient. The results are shown in Table 4.

TABLE 4

Clinical effect of Compound No. 12 in patients with ulcerative colitis

| Case (Age) | Dosage & Adm. period | Clinical symptom Before Adm. | Clinical symptom After Adm. | Clinical judgement | Effect of combined drug 3 months before Adm. |
|---|---|---|---|---|---|
| 1. Female (29) | 3 tablets /day 3 months | Diarrhoea 5–6 times Bloody stool(+++) Stomach pain(+) | Diarrhoea 2–3 times Bloody stool(−) Stomach pain(−) | Remarkable | None*) |
| 2. Male (28) | 3 tablets /day 3 months | Diarrhoea 2 times Bloody stool(+) | Soft to normal stool 1–2 times Bloody stool(−) | Effective | None*) |
| 3. Female (46) | 3 tablets /day 3 months | Bloody stool(+) Mucous stool(+) | Bloody stool(−) Mucous stool(−) | Effective | None*) |
| 4. Male (21) | 6 tablets /day 2 months | Soft stool 4–5 times Bloody stool(++) Muscous stool(+) | Normal stool once Bloody stool(−) Mucous stool(−) | Remarkable | Not combined (initial admin.) |
| 5. Female (24) | 6 tablets /day 1–5 months | Diarrhea 4–5 times Bloody stool(++) | Soft stool 1–2 times Bloody stool(+) | Remarkable | None*) |

\*)Six tablets (3.0 g) a day of sulfasalazine were administered.

As shown in the table above, the effect of Compound No. 12 was noted to be remarkable in 3 cases and effective in 2 cases. Neither unchanged, nor aggravated cases were observed and no cases with adverse reaction were observed.

In the four cases where no improvement had been observed even after administration of sulfasalazine at a daily dosage of 6 tablets (3.0 g) for 3 months, administration of Compound No. 12 at a daily dosage of from 3 to 6 tablets for from 1.5 to 3 months brought about 2 remarkable cases and 2 effective cases. Compound No. 12 was proved to show a more excellent therapeutic effect than sulfasalazine.

TEST EXAMPLE 3

Clinical Effect in Patients with Crohn's Disease

Compound No. 12 was administered to 3 patients with Crohn's disease (active stage) at a daily dosage of 6 tablets (480 mg) divided into 3 doses. The patients were 1 female and 2 males from 28 to 44 years old. Among these patients, 2 cases had not been improved even after administration of 6 tablets (3.0 g) a day of sulfasalazine for 3 months, and 1 case had not been improved even after combined administration of 6 tablets (3.0 g) a day of sulfasalazine, 6 tablets (3.0 g) a day of camostat mesilate and 6 tablets (3.0 g) a day of cepharanthine for 3 months. The results are shown in Table 5.

TABLE 5

Clinical effect of Compound No. 12 in patients with Crohn's disease

| Case (Age) | Dosage & Adm. period | Clinical symptom Before Adm. | Clinical symptom After Adm. | Clinical judgement | Effect of combined drug 3 months before Adm. |
|---|---|---|---|---|---|
| 1. Male (44) | 6 tablets /day 1–5 months | Diarrhoea 2 times Bloody stool(−) Stomach pain(++) | Soft stool 2 times Bloody stool(−) Stomach pain(−) | Effective | None*⁾ |
| 2. Male (28) | 6 tablets /day 6 months | Diarrhoea 2–3 times Stomach pain 2–3 times /day | Normal stool 1–2 times Stomach pain 0–1 times /day | Remarkable | None**⁾ |
| 3. Female (44) | 6 tablets /day 3 months | Recto-vaginal fistula CRP (++)***⁾ Eryth. sed. rate 35/h | Perfect recovery CRP (−)***⁾ Eryth. sed. rate 12/h | Remarkable | None*⁾ |

*⁾Six tablets (3.0 g) a day of sulfasalazine were administered for 3 months.
**⁾Six tablets (3.0 g) a day of sulfasalazine, 6 tablets a day of camostat masilate and 6 mg a day of cepharanthine were administered in combination for 3 months.
***⁾C reactive protein.

As shown in Table 5, the effect of Compound No. 12 was observed to be remarkable in 2 cases and effective in 1 case.

In the two cases where no improvement had been observed even after administration of sulfasalazine at a daily dosage of 6 tablets (3.0 g) for 3 months, administration of Compound No. 12 at a daily dosage of 6 tablets for from 1.5 to 3 months brought about 1 remarkable case and 1 effective case. In addition, in the case where no improvement had been observed even after combined administration of sulfasalazine at a daily dosage of 6 tablets (3.0 g), 6 tablets (3.0 g) a day of camostat mesilate and 6 mg a day of cepharanthine, administration of Compound No. 12 at a daily dosage of 6 tablets for 6 months brought about remarkable improvement. Compound No. 12 was proved to show a more excellent therapeutic effect than sulfasalazine.

From the fact that rectrovaginal fistula was closed by administration of Compound No. 12, this compound may be effective for the therapy of fistula such as internal fistula or outer fistula.

TEST EXAMPLE 4

Clinical Effect in a Patient with Behcet Syndrome

Compound No. 12 was administered to a patient with Behcet syndrome (active stage) at a daily dosage of 6 tablets (480 mg) divided into 3 doses. The patient was a 51 years old female with the main three symptoms of Behcet syndrome, pudendal ulceration, recurrent stomatitis and erythema nodosum of the legs, accompanied by multiple apthous ulceration throughout the intestinal tract. Even after combined administration of sulfasalazine at a daily dosage of 6 tablets (3.0 g) and cepharanthine at a daily dosage of 6 mg for 3 months, diarrhoea, stomach pain and stomatitis had been observed.

The results are shown in Table 6.

TABLE 6

Clinical effect of Compound No. 12 in patients with Behcet disease

| Case (Age) | Dosage & Adm. period | Clinical symptom Before Adm. | Clinical symptom After Adm. | Clinical judgement | Effect of combined drug 3 months before Adm. |
|---|---|---|---|---|---|
| 1. Female (51) | 6 tablets /day 3 months | Stomatitis (+) Diarrhoea (+) Stomach pain(+) Bloody stool(−) | Stomatitis (−) Diarrhoea (−) Stomach pain(−) Bloody stool(−) | Remarkable | None*⁾ |

*⁾Six tablets (3.0 g) a day of sulfasalazine together with 6 mg a day of cepharanthine were administered for 3 months.

As shown in Table 6, the effect of Compound No. 12 was found to be remarkable. Additionally, this compound was effective on stomatitis.

PREPARATION EXAMPLE 1

| Capsule preparation | |
|---|---|
| Compound No. 12 | 20.0 mg |
| Lactose | 108.0 mg |
| Corn starch | 70.0 mg |
| Magnesium metasilicate aluminate | 50.0 mg |
| Magnesium stearate | 2.0 mg |
| | 250 mg |

A powder containing the above components is mixed, filtered through a sieve of 60 mesh and then incorporated in a No. 2 gelatine capsule for 250 mg to obtain the desired capsule preparation.

PREPARATION EXAMPLE 2

| Tablet prepation | |
|---|---|
| Compound No. 12 | 20.0 mg |
| Lactose | 103.0 mg |
| Low-substituted hydroxypropylcellulose | 50.0 mg |
| Corn starch | 25.0 mg |
| Magnesium metasilicate aluminate | 50.0 mg |
| Magnesium stearate | 2.0 mg |
| | 250 mg |

A powder containing the above components is mixed and tableted by use of a tableting machine to obtain the aimed 250 mg tablet preparation.

If necessary, this tablet can be covered with a sugar coating.

I claim:

1. A method for the prophylaxis or therapy of diseases which are amenable to the inhibition of inflammatory cytokine formation, said method comprising administering an effective amount, to a patient in need thereof, of a polyprenyl having the following formula, as the active ingredient:

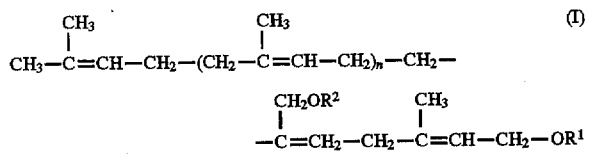

where $R^1$ and $R^2$ are the same or different, and each represents a hydrogen atom, a $C_1$–$C_4$ alkyl group, a $C_2$–$C_{12}$ aliphatic acyl group, a $C_7$–$C_{11}$ aromatic acyl group or a $C_8$–$C_{12}$ aryl-substituted aliphatic acyl group; and n represents an integer from 0 to 2.

2. The method for the prophylaxis or therapy of diseases, according to claim 1, in which the active ingredient is a polyprenyl derivative wherein $R^1$ and $R^2$ are the same, and each represents a hydrogen atom, a methyl group, a $C_2$–$C_{12}$ aliphatic acyl group, a benzoyl group or a cinnamoyl group.

3. The method for the prophylaxis or therapy of diseases, according to claim 1, in which the active ingredient is a polyprenyl derivative wherein $R^1$ and $R^2$ are the same, and each represents a hydrogen atom or a $C_2$–$C_6$ aliphatic acyl group.

4. The method for the prophylaxis or therapy of diseases, according to claim 1, in which the active ingredient is a polyprenyl derivative wherein $R^1$ and $R^2$ are the same, and each represents a hydrogen atom or an acetyl group.

5. The method for the prophylaxis or therapy of diseases, according to claim 1, in which the active ingredient is a polyprenyl derivative wherein each of $R^1$ and $R^2$ is a hydrogen atom.

6. The method for the prophylaxis or therapy of diseases, according to claim 1, in which the active ingredient is a polyprenyl derivative wherein n is 1.

7. The method for the prophylaxis or therapy of diseases, according to claim 1, in which the active ingredient is a polyprenyl derivative wherein $R^1$ and $R^2$ are the same, and each represents a hydrogen atom or an acetyl group; and n is 1.

8. The method for the prophylaxis or therapy of diseases, according to claim 1, in which the active ingredient is a polyprenyl derivative wherein each of $R^1$ and $R^2$ is a hydrogen atom and n is 1.

9. A method for the prophylaxis or therapy of ulcerative colitis, comprising administering an effective amount, to a patient in need thereof, of a polyprenyl derivatives having the following formula, as the active ingredient:

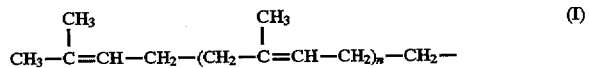

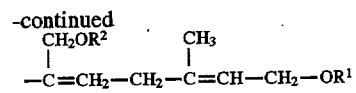

where $R^1$ and $R^2$ are the same or different, and each represents a hydrogen atom, a $C_1$–$C_4$ alkyl group, a $C_2$–$C_{12}$ aliphatic acyl group, a $C_7$–$C_{11}$ aromatic acyl group or a $C_8$–$C_{12}$ aryl-substituted aliphatic acyl group; and n represents an integer from 0 to 2.

10. The method for the prophylaxis or therapy of ulcerative colitis according to claim 9, in which the active ingredient is a polyprenyl derivative wherein $R^1$ and $R^2$ are the same, and each represents a hydrogen atom, a methyl group, a $C_2$–$C_{12}$ aliphatic acyl group, a bezoyl group or a cinnamoyl group.

11. The method for the prophylaxis or therapy of ulcerative colitis according to claim 9, in which the active ingredient is a polyprenyl derivative wherein $R^1$ and $R^2$ are the same, and each represents a hydrogen atom or a $C_2$–$C_6$ aliphatic acyl group.

12. The method for the prophylaxis or therapy of ulcerative colitis according to claim 9, in which the active ingredient is a polyprenyl derivative wherein $R^1$ and $R^2$ are the same, and each represents a hydrogen atom or an acetyl group.

13. The method for the prophylaxis or therapy of ulcerative colitis according to claim 9, in which the active ingredient is a polyprenyl derivative wherein each of $R^1$ and $R^2$ is a hydrogen atom.

14. The method for the prophylaxis or therapy of ulcerative colitis according to claim 9, in which the active ingredient is a polyprenyl derivative wherein n is 1.

15. The method for the prophylaxis or therapy of ulcerative colitis according to claim 9, in which the active ingredient is a polyprenyl derivative wherein $R^1$ and $R^2$ are the same, and each represents a hydrogen atom or an acetyl group; and n is 1.

16. The method for the prophylaxis or therapy of ulcerative colitis according to claim 9, in which the active ingredient is a polyprenyl derivative wherein each of $R^1$ and $R^2$ is a hydrogen atom and n is 1.

17. The method for the prophylaxis or therapy of ulcerative colitis according to claim 9, in which the active ingredient is a polyprenyl derivative wherein each of $R^1$ and $R^2$ is a hydrogen atom and n is 1.

* * * * *